United States Patent
Magara et al.

[11] Patent Number: 5,873,943
[45] Date of Patent: Feb. 23, 1999

[54] PROCESS FOR MANUFACTURING CRYSTALLINE MALTITOL AND CRYSTALLINE MIXTURE SOLID CONTAINING THE SAME

[75] Inventors: Mitsuo Magara, Shizuoka; Koichi Kataura, Saitama; Yoshiaki Tateno; Yoshimasa Onuki, both of Shizuoka; Yuji Osada, Saitama; Fumito Yamazaki, Shizuoka; Kazuaki Kato, Saitama, all of Japan

[73] Assignee: Towa Chemical Industry Co., Ltd., Tokyo, Japan

[21] Appl. No.: 643,157

[22] Filed: May 2, 1996

[30] Foreign Application Priority Data

May 2, 1995 [JP] Japan .................................. 7-131194
Feb. 1, 1996 [JP] Japan .................................. 8-037074

[51] Int. Cl.$^6$ ............................ C08B 30/00; C13K 1/06; C13F 1/02; C07G 17/00
[52] U.S. Cl. .............................. 127/29; 127/30; 127/40; 127/58; 127/60; 127/61; 426/658; 536/124; 536/127
[58] Field of Search .................... 127/40, 29, 58, 127/30, 61, 60; 426/658; 536/124, 127

[56] References Cited

U.S. PATENT DOCUMENTS

| | | | |
|---|---|---|---|
| 4,408,041 | 10/1983 | Hirao et al. | 536/4.1 |
| 4,717,765 | 1/1988 | Hirao et al. | 536/124 |
| 4,789,559 | 12/1988 | Hirao et al. | 426/658 |
| 4,846,139 | 7/1989 | Devos et al. | 127/40 |
| 4,849,023 | 7/1989 | Devos et al. | 127/40 |
| 5,304,388 | 4/1994 | Ueno et al. | 426/658 |
| 5,354,856 | 10/1994 | Kawashima et al. | 536/127 |
| 5,583,215 | 12/1996 | Kawashima et al. | 536/127 |

*Primary Examiner*—Mark L. Bell
*Assistant Examiner*—Patricia L. Hailey
*Attorney, Agent, or Firm*—Beveridge, DeGrandi, Weilacher & Young, LLP

[57] ABSTRACT

To provide an economically advantageous process for manufacturing crystalline maltitol and crystalline mixture solid containing crystalline maltitol. The process of this invention uses the syrup having a maltose purity of 81 to 90% as the starting material. The syrup is hydrogenated under the existence of catalyst, and then subjected to a chromatographic separation by using cation-exchange resin, resulting in an aqueous solution of maltitol having a maltitol purity of 94 to 99.9%. The aqueous solution, is further crystallized in the presence of a seed crystal, subjected to a separation, cooled and kneaded so as to manufacture both crystalline maltitol and crystalline mixture solid containing crystalline maltitol at the same time.

10 Claims, No Drawings

PROCESS FOR MANUFACTURING CRYSTALLINE MALTITOL AND CRYSTALLINE MIXTURE SOLID CONTAINING THE SAME

DETAILED EXPLANATION OF INVENTION

1. Field of Invention

This invention is concerned with a process for manufacturing a crystalline maltitol and a crystalline mixture solid containing the same. Particularly, this invention intends to provide a process for manufacturing a crystalline maltitol and crystalline mixture solid containing the maltitol from the same law material.

2. Prior Art and Problems Solved by the Invention

A crystalline maltitol and crystalline mixture solid containing crystalline maltitol are sugar alcohol which is prepared by hydrogenating maltose under the existence of catalyst and crystallizing or solidifying the same. The sweet taste of the crystalline maltitol and crystalline mixture solid containing the maltitol is similar to that of sugar and their sweetness is more similar to sucrose than other sugar alcohol. It is very little for the crystalline maltitol and crystalline mixture solid containing crystalline maltitol to be utilized by oral bacteria and thus hardly cause a tooth decay. They are also poorly digestible by human digestive enzymes. Because of these features, a crystalline maltitol and crystalline mixture solid containing the maltitol are widely used by diabetics, people who are on diet and people who want to prevent tooth decay.

Further, because a crystalline maltitol and crystalline mixture solid containing crystalline maltitol have various beneficial functions such as low hygroscopicity, stability against the heat, no promotion of insulin secretion and preferable influence in absorption of various minerals, their use is not restricted to the particular uses discussed above. They are coming into common use as a material for general food, pharmaceuticals, and cosmetics.

The technology for manufacturing a crystalline maltitol is publicly known. For example, the technology is disclosed in (1) Tokkyo Kokai Koho (Patent Laid Open Publication) Showa 57(1982)-134498 and (2) Tokkyo Kokai Koho (Patent Laid Open Publication) Showa 61(1986)-180797.

For example, the publication (1) discloses a process for preparing a maltose whose maltose purity is 93 to 100% by weight for solid material in the solid component (hereinafter, this unit may be indicated merely as "%"), including steps of liquefying an underground starch such as potato starch into low DE (dextrose equivalent) by liquefying enzyme, saccharifying it by reacting with debranching enzymes, such as β-amylase and isoamylase, purifying it and crystallizing maltose if it is necessary.

In turn, the maltose is hydrogenated under the existence of catalyst to manufacture a high purity maltitol. The maltitol is separated when massecuite is generated through the crystallization, resulting in a crystalline maltitol. This method is discussed in the above publication.

Further, the publication (2) discloses a technology that a maltose syrup whose concentration is 25 to 45% and whose maltose purity is 50 to 80% in the solid component is hydrogenated under the existence of catalyst to obtain corresponding maltitol. The maltitol is chromatographically separated to obtain a fraction whose maltitol purity is more than 87% by weight in the solid component. The maltitol is further condensed to have the concentration within the range of 75 to 92%, and is crystallized. The crystalline maltitol is recovered and its mother liquor are again subjected to the chromatographic separation step.

A process for manufacturing crystalline mixture solid containing crystalline maltitol is also publicly known. For example, one process is disclosed in the publication (1).

The publication (1) discussed above discloses a process for manufacturing crystalline mixture solid containing crystalline maltitol from a generated massecuite by a publicly known method such as a block grinding method, a fluidized drying method, and the spray-drying method.

The respective prior art processes are, however, found to have problems.

For example, according to the process disclosed in the publication (1), in the step of liquefying starch, a solution having a low DE needs to be produced to be saccharified. Because the use of a normal concentration solution results in a high viscosity, liquefaction and saccharification must be conducted using a low concentration solution although the use of such solution is economically disadvantageous.

Further, in the saccharification, a great amount of enzyme is required and expensive isoamylase must be used.

Further, the best purity of maltose obtained by the saccharification is limited to 90 to 93%. When a crystallization process is added to improve the maltose purity, the cost for the entire process is further increased. Therefore, this process involves problems which make the process economically disadvantageous.

Furthermore, in the catalytic hydrogenation step, a great amount of catalyst must be used in the condition where a temperature is stable to control the decomposition of maltose or maltitol so as to maintain a high purity of maltitol. This also makes the process economically disadvantageous.

Additionally, the process for manufacturing crystalline maltitol disclosed in the publication (1) includes a step for crystallizing and separating an aqueous solution of maltitol having, normally, a maltitol purity of about 92% in the solid component. The step results in a great amount of molasses, but it is difficult to recrystallize the molasses. These molasses can be only used to sell as inexpensive liquid products to which high value cannot be added, such as hydrogenated maltose syrup or hydrogenated starch hydrolysates. In this respect, the process involves a problem of being economically disadvantageous.

In turn, the process disclosed in the publication (2) involves a problem that a chromatographic separation of each component is difficult even after a catalytic hydrogenation is conducted because syrup containing maltose of about 50 to 80% includes a considerable amount of glucose and origosaccharide. Thus, if a syrup is subjected to a chromatographic separation to obtain a high purity maltitol, the effectiveness of separation is poor. In other words, the yield of a high purity maltitol is low. An improvement of the separation effectiveness results in a syrup having a low purity maltitol, which makes the subsequent crystallization step difficult to conduct. The improvement of effectiveness also increase the amount of a low content maltitol syrup which is a by-product of the chromatographic separation step. This syrup of by-product is not used for a product to which high value can be added. In short, this process is also economically disadvantageous.

The publication (1) also discloses a process for manufacturing crystalline mixture solid containing crystalline maltitol. The process inherently has a problem because, as discussed above, a step involved in the process for preparing. maltose is economically disadvantageous.

In short, a prior process art for manufacturing crystalline maltitol and crystalline mixture solid containing the same is significantly more expensive than those for processing other sugar alcohol for a general use such as sorbitol. Therefore, a development of means to solve these problems, in other words, a development of an economically advantageous process, has been long desired.

DISCLOSURE OF THE INVENTION

Inventors of this invention reviewed said problems carefully and found out that syrup having a maltose purity of 81 to 90% which is provided by saccharification by enzyme of a general use after starch is liquefied can be relatively inexpensively prepared. Thus, they used this syrup having a maltose purity of 81 to 90% as the starting material, and it is chromatographically separated by using cation-exchange resin after the syrup is hydrogenated under the existence of catalyst. Because of that, they succeed to prepare an aqueous solution of maltitol having a maltitol purity of 92 to 99.9%, preferably 94 to 99.9%. The solution is further crystallized in the presence of a seed crystal, centrifuged, cooled and kneaded. As a result, a process for manufacturing both crystalline maltitol and crystalline mixture solid containing crystalline maltitol at the same time is provided. Additionally, the inventors succeeded to manufacture crystalline mixture solid containing crystalline maltitol by adding a seed crystal after the crystalline mixture solid was crystallized, cooling and kneading it. Thus, they solved the problems inherent to the prior art and completed this invention.

Means to solve the problem of this invention are as follows:

The first invention is:

a process for manufacturing crystalline maltitol and crystalline mixture solid containing the maltitol, characterized in that the process passes sequentially through the following processes:

1) the first step of hydrogenating syrup having a concentration of 30 to 75% by weight and a maltose content of 81 to 90% by weight in the solid component under the existence of catalyst to obtain corresponding syrup of sugar alcohol;

2) the second step of chromatographically separating said syrup of sugar alcohol by supplying said syrup of sugar alcohol to a column packed with cation-exchange resin to obtain high content maltitol syrup fraction having a maltitol purity of 92 to 99.9% by weight in the solid component; and 3) the third step having a sub-step of crystallizing, in the presence of a seed crystal, a part of syrup resulting from condensation of said high content maltitol syrup fraction to collect crystalline maltitol, and another sub-step of spray-drying or cooling and kneading, in the presence of a seed crystal, remaining part to obtain crystalline mixture solid containing crystalline maltitol.

The second invention is:

a process for manufacturing crystalline maltitol and crystalline mixture solid containing the maltitol, characterized in that the process passes sequentially through the following processes:

1) the first step of hydrogenating syrup having a concentration of 30 to 75% by weight and a maltose content of 81 to 90% by weight in the solid component under the existence of catalyst to obtain corresponding syrup of sugar alcohol;

2) the second step of chromatographically separating said syrup of sugar alcohol by supplying said syrup of sugar alcohol to a column packed with cation-exchange resin to obtain high content maltitol syrup fraction having a maltitol purity of 92 to 99.9%, preferably 94 to 99.9%, by weight in the solid component;

3) the third step of crystallizing after a condensation of said high content maltitol syrup fraction and separating crystalline maltitol from mother liquor, whereby collecting crystalline maltitol; and 4) the forth step of adding said high content maltitol syrup fraction resulting from the second step to said mother liquor resulting from the third step, condensing and spray-drying or cooling and kneading it in the presence of a seed crystal to obtain crystalline mixture solid containing crystalline maltitol.

The third invention is:

a process for manufacturing crystalline maltitol and crystalline mixture solid containing the maltitol, characterized in that the process passes sequentially through the following processes:

1) the first step of hydrogenating syrup having a concentration of 30 to 75% by weight and a maltose content of 81 to 90% by weight in the solid component under the existence of catalyst to obtain corresponding syrup of sugar alcohol;

2) the second step of chromatographically separating said syrup of sugar alcohol by supplying said syrup of sugar alcohol to a column packed with cation-exchange resin to obtain high content maltitol syrup fraction having a maltitol purity of 92 to 99.9%, preferably 94 to 99.9%, by weight in the solid component;

3) the third step of crystallizing after a condensation of said high content maltitol syrup fraction and separating crystalline maltitol from mother liquor, whereby collecting crystalline maltitol; and 4) the fourth step of adding a seed crystal to said mother liquor resulting from the third step, and spray-drying or cooling and kneading to obtain crystalline mixture solid containing crystalline maltitol.

The fourth invention is:

in either process of said first, second and third inventions, said cation-exchange resin is either charged with calcium ion or sodium ion and said chromatographic separation is batch process type.

A maltose syrup having a maltose purity in the range of 81 to 90% in the solid component can be used as the starting material of this invention. The syrup can be made from any starch, including corn starch and potato starch.

In consideration of the object of this invention, the inexpensive cost for process and material is very important factor. The syrup should be prepared from a starch using relatively inexpensive general use enzyme such as α-amylase, β-amylase, and pullulanase. Syrup containing little amount of origosaccharide which is between DP=3 and DP=6 is suitable for the process of this invention because such syrup is readily used in the second and subsequent steps, i.e., chromatographic separation, crystallization-separation and cooling-kneading-solidification steps.

If the maltose purity is less than 81% in the solid component of syrup, other components are readily mixed with the maltitol fraction during the chromatographic separation step. In case where a high purity maltitol fraction is required, the amount of a collectable high content maltitol fraction results in considerably low, which makes the entire process economically disadvantageous. The use of such low purity maltose syrup makes difficult to obtain a high purity maltitol fraction, decreases the amount of crystalline maltitol resulting from the crystallization and separation steps, and prevents syrup from solidifying in cooling and kneading step due to insufficient amount of maltitol contained in the syrup after separation step. Because of these problems, such syrup having a purity less than 81% is not preferable for the process of this invention.

On the other hand, if syrup having a maltose purity of more than 90% in the solid component of syrup must be obtained, very expensive and peculiar enzyme such as isoamylase must be used or an expensive step of crystallizing maltose and other additional special steps must be required to obtain such high purity syrup. Accordingly, the production cost of such syrup is very expensive and cannot be compliance with the object of this invention.

The maltose starting material used in the first step of this invention preferably has a concentration of 30 to 75%. If the concentration of the maltose starting material is less than 30%, the amount to be handled significantly increases, which results in a low productivity per production line. Additionally, the cost for the subsequent step of condensing the syrup increases. Thus, a process of using a syrup having a purity of less than 30% is economically disadvantageous. In contrast, if syrup having a concentration of more than 75% is used, such syrup is difficult to be handled in the process and thus is not suitable because components which did not react resulting in the hydrogenation step increases, and filtering insoluble materials, such as catalyst, from such syrup is difficult.

The catalyst used in the first step of this invention can be used most catalysts which are usually used for hydrogenating sugar under the existence of catalyst. In particular, commercially available Raney nickel catalyst, and reactivatable precious metal catalysts, such as powder Raney nickel and lump Raney nickel, and ruthenium catalyst carried by activated carbon are preferably used.

Any condition which does not significantly decompose maltose can be chosen for the hydrogenation step in the process of this invention. Usually, the hydrogenation step preferably is conducted under the hydrogen pressure of more than 10 kg/cm$^2$ preferably that of 50 to 200 kg/cm$^2$ and at a temperature of 90° to 150° C. so that the hydrogenation continues until the absorption of hydrogen stops.

It is preferable that the amount of non-reducing component in the syrup of sugar alcohol resulting from the hydrogenation step is small. Reduction of the amount of non-reducing component to extremely small may make the process economically disadvantageous because of the increase of catalyst amount required for the reaction step and the decomposition of maltose. The reaction step should be controlled to maintain the amount of the non-reducing component 1% or less, preferably 0.5% or less in the solid component in the syrup resulting from the hydrogenation step.

After the hydrogenation step, catalysts is removed from the resulting syrup of sugar alcohol, if it is necessary. The syrup is further decolorized and deionized by activated carbon or ion-exchange resin, if it is necessary and then proceeds to the second step.

Any commercially available cation-exchange resin is suitable to be used in the second step of this invention. In particular, a commercially available strong acid cation-exchange resin which is made of styrene-divinylbenzene bridge polymer combined with sulfonic group can be most advantageously used in the second step of this invention by charging sodium ion or calcium ion by a conventional method.

Additionally, any type of chromatography including batch process type, pseudo moving bed type, single column type or multiple column type can be used for the second step of chromatographic separation. The chromatographic separation step can adopt a publicly known method. If the amount of sorbitol fraction in the syrup of sugar alcohol applied to the chromatographic separation step results in sufficiently small, a multiple column and pseudo moving bed type chromatography is most suitable. If the amount of sorbitol fraction in the syrup of sugar alcohol is relatively significant, the purity of high content maltitol syrup fraction may not be sufficiently high even if the fraction of more than DP=3 is removed. If the purity is not sufficiently high, batch process type is preferable because it can remove sorbitol faction.

Conditions for the chromatographic separation is selected so that the maltitol in the high content maltitol syrup resulting from the second step is adjusted to have a content of 92 to 99.9%, preferably 94 to 99.9%, in the solid component. If the maltitol content is less than 92%, crystallization in the crystallization step is often difficult, resulting in a low crystal yield. Further, such syrup is difficult to be solidified in the spray-drying step or in the cooling and kneading step. Therefore, such syrup is not suitable. If a syrup having a purity of more than 99.9% is separated, the amount of such high content maltitol syrup resulting from the chromatographic separation is very small. Thus, the separation of such high concentration maltitol syrup is economically meaningless.

In the third step of this invention, after condensing a high content maltitol syrup fraction, a portion of the syrup is crystallized and separated while spray-drying or cooling and kneading the remaining portion of the condensed high content maltitol syrup to obtain crystalline maltitol as well as a crystalline mixture solid containing the crystalline maltitol. Not completely removing water in the condensation is essential to proceed crystallization. The preferable concentration in the crystallization step and the separation step is 60 to 90% and the preferable concentration in the spray-drying step or cooling and kneading step is 90 to 99%.

The crystallization and separation which are part of the third step of this invention are conducted by providing crystalline maltitol or crystalline mixture solid containing the maltitol as a seed crystal in over-saturated high content maltitol syrup so as to crystallize maltitol and to separate molasses from crystalline, for example, by a centrifugal separator.

Further, the spray-drying or cooling and kneading which is the other part of the third step of this invention is conducted by providing crystalline maltitol or crystalline mixture solid containing the maltitol as a seed crystal in over-saturated high content maltitol syrup to crystallize maltitol, and then spray-drying or cooling and kneading by a kneader or an extruder, solidifying, drying and crashing.

According to one preferred aspect of this invention, the mother liquor resulting from the third step and the high content maltitol syrup resulting from the second step are mixed and condensed. In turn, crystalline maltitol or crystalline mixture solid containing crystalline maltitol is provided as a seed crystal in the condensed syrup which is in turn cooled and kneaded to obtain crystalline mixture solid containing crystalline maltitol to which high value can be added. In this process, as discussed above, a syrup containing maltose of 81 to 90% in the solid component is used as the starting material. The syrup is subjected to a chromatographic separation step so as to obtain a high content maltitol syrup containing a maltitol content of 92 to 99.9%, preferably 94 to 99.9%, in the solid component. The resulting high content maltitol syrup is mixed with the mother liquor resulting from a crystallization and separation step. Following these steps, this invention makes it possible for the first time to provide such valuable crystalline mixture solid containing crystalline maltitol.

In this preferred aspect, the mother liquor resulting from the third step and the high content maltitol syrup resulting from the second step can be mixed at any ratio acceptable to produce and solidify crystalline mixture solid containing crystalline maltitol. The mixture is most preferably prepared to include solid component in the mother liquor and the solid component of the high content maltitol syrup at a ratio of 1:0.2 to 5.

According to another preferred aspect of this invention, the mother liquor resulting from the third step is condensed as it is necessary. Crystalline maltitol or crystalline mixture solid containing the maltitol is added as a seed crystal in the condensed mother liquor. The liquor is further subjected to a cooling and kneading step to obtain crystalline mixture solid containing crystalline maltitol to which high value can be added. In this process, as discussed above, a syrup containing maltose of 81 to 90% in the solid component is used as the starting material. The syrup is subjected to a chromatographic separation step so as to obtain a high content maltitol syrup containing a maltitol content of 92 to 99.9%, preferably 94 to 99.9%, in the solid component. The resulting high content maltitol syrup is condensed and crystallized to obtain crystalline maltitol and mother liquor. Seed crystal of crystalline maltitol or crystalline mixture solid containing maltitol is added to the mother liquor obtained from the crystallization and separation step and subjected to a cooling and kneading step to obtain additional crystalline mixture solid containing maltitol. Following these steps, this invention makes it possible for the first time to provide such valuable crystalline mixture solid containing crystalline maltitol.

As discussed above, this invention makes it possible to manufacture both crystalline maltitol and crystalline mixture solid containing crystalline maltitol to which high value can be added at the same time from inexpensive syrup having a maltose purity of 81 to 90% in the solid component manufactured by using enzyme of general use. Because the manufacturing process of this invention results in little by-product to which high value cannot be added and the separation effectiveness in the chromatographic separation step is very high, the cost for condensing the syrup is decreased. As a result, according to this invention, crystalline maltitol and crystalline mixture solid containing crystalline maltitol can be manufactured less expensively than those manufactured by a conventional process.

PREFERRED EXAMPLES

This invention is further discussed below in detail by making reference to test examples and examples. The technical scope of this invention is not, however, limited by the explanation which will be discussed below.

In the examples which will be discussed below, unless it is specifically indicated otherwise, % indicates % by weight.

EXAMPLE 1
<First Step>

A commercially available aqueous solution of high purity maltose (mfd. by NIHON SHOKUHIN KAKO K.K., concentration: 65%, sugar composition in the solid component: maltose: 87.7%, glucose: 8.1%, sugar of equal or more than DP3: 4.2%) was reduced under the existence of Raney nickel catalyst at a hydrogen pressure of 100 kg/cm$^2$ and 130° C. for 1 hour, to obtain aqueous solution of maltitol. The sugar composition in the solid component of the resulting aqueous solution of maltitol was that maltitol was 87.4%, sorbitol was 8.4%, sugar alcohol which was equal or more than DP3 was 4.2%.

<Second Step>

The aqueous solution of maltitol resulting from the first step was adjusted to have a concentration of 50% and a temperature of 60° C. 20 l of the solution was supplied to the first column of serially connected four columns. The height of the columns was 1 m and each column was packed with 25 l of cation-exchange resin charged with sodium. The solution was provided to pass through the first to forth column at superficial velocity in a column (SV)=0.5. The solution was finally extruded from the column using water as eluent to recover a fraction having a high purity of maltitol. As a result, a high content maltitol syrup was obtained.

The amount of solid component in the resulting high content maltitol syrup was 85.7% when the amount of solid component in the aqueous solution of maltitol supplied to the columns was 100%. Sugar composition in the solid component included 95.8% of maltitol, 1.4% of sorbitol, 2.8% of origosaccharide alcohol which was equal or more than DP=3.

Further, the solid component in the other fractions was 14.3% when the amount of solid component in the aqueous solution of maltitol supplied to the column was 100%. Sugar composition in the solid component included 37.1% of maltitol, 50.3% of sorbitol, 12.6% of origosaccharide alcohol which was equal or more than DP=3.

<Third Step>

After the high content maltitol syrup resulting from the second step was condensed to have the concentration of 79%, a portion of the condensed syrup was taken out. Crystalline maltitol powder the amount of which was 0.2% in proportion to the solid component in the syrup was added to the portion under a condition at 64° C. The syrup was slowly stirred and cooled to decrease the temperature from 64° C. to 20° C., spending 24 hours, resulting in magma. The syrup was then separated by a centrifuge. The resulting crystals were rinsed by a small amount of water to recover the crystals.

The purity of crystal was 99.4% and the crystal yield was 41.4% when the solid component in the high content maltitol syrup was 100%.

The concentration of the resulting molasses was 69.9%. The sugar composition included 93.2% of maltitol, 2.4% of sorbitol, 4.4% of origosaccharide alcohol which was equal or more than DP=3.

In turn, the remaining portion of the high content maltitol syrup resulting from the second step was condensed to have the concentration of 95%. The syrup was set at a temperature of 120° C. and then supplied to a twin-screw extruder for foods (mfg. by NIHON SEIKOSHO K.K., TEX38FSS-20AW-V) at a rate of 22 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol.

The purity of said crystalline mixture solid obtained was 95.7%.

When the high content maltitol syrup used in the third step was divided into two portions, one portion being used for the separation step and the other portion being used for manufacturing crystalline mixture solid powder containing crystalline maltitol, the yield for the product to which high value can be added was 70.7% in the solid component when the solid component in the high content maltitol syrup resulting from the second step was 100%. This yield was significantly higher than those of conventional processes.

EXAMPLE 2

<First Step>

A commercially available aqueous solution of high purity maltose (mfg. by NIHON SHOKUHIN KAKO K.K., concentration: 60%, sugar composition in the solid component: maltose: 81.2%, glucose: 0.3%, sugar of equal or more than DP3: 18.5%) was reduced under the existence of Raney nickel catalyst at a hydrogen pressure of 100 kg/cm$^2$ and 130° C. for 60 minutes, to obtain aqueous solution of maltitol.

The sugar composition in the solid component of the resulting aqueous solution of maltitol was that maltitol was 81.0%, sorbitol was 0.5%, sugar alcohol which was equal or more than DP3 was 18.5%.

<Second Step>

The aqueous solution of maltitol resulting from the first step was adjusted to have a concentration of 50% and a temperature of 60° C. 20 l of the solution was supplied to a column. The height of the column was 0.8 m and the column was packed with 20 l of cation-exchange resin charged with sodium. The solution was provided to pass through the column at superficial velocity in a column (SV)=0.4. The solution was finally extruded from the column using water as eluent to recover a fraction having a high purity of maltitol. As a result, a high content maltitol syrup was obtained.

Sugar composition in the solid component of the resulting high content maltitol syrup included 98.0% of maltitol, 0.7% of sorbitol, 1.3% of sugar alcohol which was equal or more than DP3.

<Third Step>

After the high content maltitol syrup resulting from the second step was condensed to have the concentration of 78.5%, a portion of the condensed syrup was taken out. Crystalline maltitol powder the amount of which was 0.2% in proportion to the solid component in the syrup was added to the portion under a condition at 64° C. The syrup was slowly stirred and cooled to decrease the temperature from 64° C. to 20° C., spending 24 hours, resulting in magma. The syrup was then separated by a centrifuge. The resulting crystals were rinsed by a small amount of water to recover the crystals.

The purity of crystal was 99.8% and the crystal yield was 45.5% when the solid component in the high content maltitol syrup was 100%.

The concentration of the resulting molasses was 66.6%. The sugar component included 96.5% of maltitol, 1.7% of sorbitol, 1.8% of origosaccharide alcohol which was equal or more than DP=3.

<Fourth Step>

The molasses resulting from the third step was mixed with the remaining portion of the high content maltitol syrup resulting from the second step in a ratio of 2 to 1. The mixture was condensed to have a concentration of 95% and then adjusted to have a temperature of 121° C. It was then supplied to a twin-screw extruder for foods (mfg. by NIHON SEIKOSHO K.K., TEX38FSS-20AW-V) at a rate of 25kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 38° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol.

The purity of crystalline mixture solid obtained was 96.9%.

EXAMPLE 3

<First Step>

A commercially available aqueous solution of high purity maltose (mfg. by NIHON SHOKUHIN KAKO K.K., concentration: 60%, sugar composition in the solid component: maltose: 84.6%, glucose: 7.8%, sugar of equal or more than DP3: 7.6%) was reduced under the existence of Raney nickel catalyst at a hydrogen pressure of 130 kg/cm$^2$ and 120° C. for 1.2 hours, to obtain aqueous solution of maltitol. The sugar composition in the solid component of the resulting aqueous solution of maltitol was that maltitol was 84.4%, sorbitol was 8.0%, sugar alcohol which was equal or more than DP3 was 7.6%.

<Second Step>

The aqueous solution of maltitol resulting from the first step was adjusted to have a concentration of 50% and a temperature of 60° C. 15 l of the solution was supplied to a column. The height of the column was 0.8 m and the column was packed with 20 l of cation-exchange resin charged with sodium. The solution was provided to pass through the column at superficial velocity in a column (SV)=0.5. The solution was finally extruded from the column using water as eluent to recover a fraction having a high purity of maltitol. As a result, a high content maltitol syrup was obtained.

Sugar composition in the solid component of the resulting high content maltitol syrup included 98.2% of maltitol, 1.2% of sorbitol, 0.6% of sugar alcohol which was equal or more than DP3.

<Third Step>

After the high content maltitol syrup resulting from the second step was condensed to have the concentration of 79.5%, a portion of the condensed syrup was taken out. Crystalline maltitol powder the amount of which was 0.2% in proportion to the solid component in the syrup was added to the portion under a condition at 63° C. The syrup was slowly stirred and cooled to decrease the temperature from 63° C. to 20° C., spending 24 hours, resulting in magma. The syrup was then separated by a centrifuge. The resulting crystals were rinsed by a small amount of water to recover the crystals.

The purity of crystal was 99.8% and the crystal yield was 49.3% when the solid component in the high content maltitol syrup was 100%.

The concentration of the resulting molasses was 66.5%. The sugar composition included 96.6% of maltitol, 1.8% of sorbitol, 1.6% of oligosaccharide alcohol which was equal or more than DP=3.

<Fourth Step>

The molasses resulting from the third step was condensed to have a concentration of 95% and then adjusted to have a temperature of 120° C. It was then supplied to a twin-screw extruder for foods (mfg. by NIHON SEIKOSHO K.K., TEX38FSS-20AW-V) at a rate of 22 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol.

The purity of crystalline mixture solid obtained was 96.9%.

EXAMPLE 4

<First Step>

A commercially available aqueous solution of high purity maltose (mfg. by NIHON SHOKUHIN KAKO K.K., concentration: 65%, sugar composition in the solid component: maltose: 88.4%, glucose: 7.0%, sugar of equal or more than DP3: 4.6%) was reduced under the same conditions of the reduction step in the first step of Example 1, to obtain aqueous solution of maltitol.

The sugar composition in the solid component of the resulting aqueous solution of maltitol was that maltitol was 88.2%, sorbitol was 7.2%, sugar alcohol which was equal or more than DP3 was 4.6%.

<Second Step>

The aqueous solution of maltitol resulting from the first step was adjusted to have a concentration of 60% and a temperature of 60° C. 22 l of the solution was supplied to a column which was packed with 300 l of cation-exchange resin charged with sodium. The solution was provided to pass through the column at superficial velocity in a column (Sv)=0.4. The solution was finally extruded from the column using water as eluent to recover a fraction having a high purity of maltitol. As a result, a high content maltitol syrup was obtained.

The amount of solid component in the resulting high content maltitol syrup was 74.2% when the amount of solid component in the aqueous solution of maltitol supplied to the column was 100%. Sugar composition in the solid component included 95.1% of maltitol, 1.8% of sorbitol, 3.1% of origosaccharide alcohol which was equal or more than DP=3.

Further, the solid component in the other fractions was 25.8% when the amount of solid component in the aqueous solution of maltitol supplied to the column was 100%. Sugar composition in the solid component included 68.4% of maltitol, 22.7% of sorbitol, 8.9% of origosaccharide alcohol which was equal or more than DP=3.

<Third Step>

After the high content maltitol syrup resulting from the second step was condensed to have the concentration of 80%, a portion of the condensed syrup was taken out. Crystalline maltitol powder the amount of which was 0.2% in proportion to the solid component in the syrup was added to the portion under a condition at 63° C. The syrup was slowly stirred and cooled to decrease the temperature from 63° C. to 20° C., spending 24 hours, resulting in magma. The syrup was then separated by a centrifuge. The resulting crystals were rinsed by a small amount of water to recover the crystals.

The purity of crystal was 99.5% and the crystal yield was 52% when the solid component in the high content maltitol syrup was 100%.

The concentration of the resulting molasses was 61.4%. The sugar composition included 90.4% of maltitol, 3.5% of sorbitol, 6.1% of origosaccharide alcohol which was equal or more than DP=3.

Further, the remaining portion of the high content maltitol syrup resulting from the second step was condensed to have the concentration of 97% and then adjusted to have a temperature of 90° C. It was then supplied to a twin-screw extruder for foods (mfg. by NIHON SEIKOSHO K.K., TEX38FSS-20AW-V) at a rate of 20 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was subjected to the same steps discussed in Example 3, to obtain crystalline mixture solid powder containing crystalline maltitol. The purity of crystalline mixture solid obtained was 95%.

EXAMPLE 5

<First Step>

A commercially available aqueous solution of high purity maltose (mfd. by NIHON SHOKUHIN KAKO K.K., concentration: 60%, sugar composition in the solid component: maltose: 85.1%, glucose: 0.3%, sugar of equal or more than DP3: 14.6%) was reduced under the existence of Raney nickel catalyst at a hydrogen pressure of 150 kg/cm$^2$ and 120° C. for 120 minutes, to obtain aqueous solution of maltitol. The sugar composition in the solid component of the resulting aqueous solution of maltitol was that maltitol was 85.0%, sorbitol was 0.5%, sugar alcohol which was equal or more than DP3 was 14.5%.

<Second Step>

The aqueous solution of maltitol resulting from the first step was adjusted to have a concentration of 60%. 20 l of the solution was supplied to a column which was packed with 300 l of cation-exchange resin charged with sodium. The solution was provided to pass through the column at superficial velocity in a column (SV)=0.3. The solution was finally extruded from the column using water as eluent to recover a fraction having a high purity of maltitol. As a result, a high content maltitol syrup was obtained.

Sugar composition in the solid component of the resulting high content maltitol syrup included 98.0% of maltitol, 0.7% of sorbitol, 1.3% of sugar alcohol which was equal or more than DP3.

<Third Step>

After the high content maltitol syrup resulting from the second step was condensed to have the concentration of 78%, a portion of the condensed syrup was taken out. Crystalline maltitol powder the amount of which was 0.5% in proportion to the solid component in the syrup was added to the portion under a condition at 62° C. The syrup was slowly stirred and cooled to decrease the temperature from 62° C. to 20° C., spending 24 hours, resulting in magma. The syrup was then separated by a centrifuge. The resulting crystals were rinsed by a small amount of water to recover the crystals.

The purity of crystal was 99.8% and the crystal yield was 56% when the solid component in the high content maltitol syrup was 100%.

The concentration of the resulting molasses was 63.4%. The sugar composition included 95.6% of maltitol, 1.5% of sorbitol, 2.9% of oligosaccharide alcohol which was equal or more than DP=3.

<Fourth Step>

The molasses resulting from the third step was mixed with the remaining portion of the high content maltitol syrup resulting from the second step in a ratio of 7 to 3. The mixture was condensed to have a concentration of 97% and then adjusted to have a temperature of 90° C. It was then supplied to a twin-screw extruder for foods (mfg. by NIHON SEIKOSHO K.K., TEX38FSS-20AW-V) at a rate of 25 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was subjected to the same steps discussed in Example 3 to obtain crystalline mixture solid powder containing crystalline maltitol. The purity of crystalline mixture solid obtained was 96.5%.

EXAMPLE 6

<First Step>

A commercially available aqueous solution of high purity maltose (mfd. by NIHON SHOKUHIN KAKO K.K., concentration: 60%, sugar composition in the solid component: maltose: 81.6%, glucose: 1.5%, sugar of equal or more than DP3: 16.9%) was reduced under the existence of Raney nickel catalyst at a hydrogen pressure of 100 kg/cm$^2$ and 130° C. for 120 minutes, to obtain aqueous solution of maltitol.

The sugar composition in the solid component of the resulting aqueous solution of maltitol was that maltitol was 81.2%, sorbitol was 1.9%, sugar alcohol which was equal or more than DP3 was 16.9%.

<Second Step>

The aqueous solution of maltitol resulting from the first step was adjusted to have a concentration of 60% and a temperature of 60° C. 22 l of the solution was supplied to a column which was packed with 300 l of cation-exchange resin charged with sodium. The solution was provided to pass through the column at superficial velocity in a column (SV)=0.3. The solution was finally extruded from the column using water as eluent to recover a fraction having a high purity of maltitol. As a result, a high content maltitol syrup was obtained.

Sugar composition in the solid component of the resulting high content maltitol syrup included 97.6% of maltitol, 0.5% of sorbitol, 1.9% of sugar alcohol which was equal or more than DP3.

<Third Step>

After the high content maltitol syrup resulting from the second step was condensed to have the concentration of 82%, a portion of the condensed syrup was taken out. Crystalline maltitol powder the amount of which was 0.15% in proportion to the solid component in the syrup was added to the portion under a condition at 65° C. The syrup was slowly stirred and cooled to decrease the temperature from 65° C. to 25° C., spending 24 hours, resulting in magma. The syrup was then separated by a centrifuge. The resulting crystals were rinsed by a small amount of water to recover the crystals.

The purity of crystal was 99.6% and the crystal yield was 54% when the solid component in the high content maltitol syrup was 100%.

The concentration of the resulting molasses was 67.4%. The sugar composition included 95.3% of maltitol, 1.0% of sorbitol, 3.7% of oligosaccharide alcohol which was equal or more than DP=3.

<Fourth Step>

Further, the molasses resulting from the third step was condensed to have a concentration of 97% and then adjusted to have a temperature of 90° C. It was then supplied to a twin-screw extruder for foods (mfg. by NIHON SEIKOSHO K.K., TEX38FSS-20AW-V) at a rate of 25 kg /hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol. The purity of crystalline mixture solid obtained was 95.2%.

EXAMPLE 7

<First Step>

A commercially available aqueous solution of high purity maltose (mfd. by NIHON SHOKUHIN KAKO K.K., concentration: 65%, sugar composition in the solid component: maltose: 87.2%, glucose: 4.1%, sugar of equal or more than DP3: 8.7%) was reduced under the existence of Raney nickel catalyst at a hydrogen pressure of 100 kg/cm$^2$ and 130° C. for 1 hour, to obtain aqueous solution of maltitol. The sugar composition in the solid component of the resulting aqueous solution of maltitol was that maltitol was 87.0%, sorbitol was 4.3%, sugar alcohol which was equal or more than DP3 was 8.7%.

<Second Step>

The aqueous solution of maltitol resulting from the first step was adjusted to have a concentration of 50% and a temperature of 60° C. 20 l of the solution was supplied to the first column of serially connected four columns. The height of the columns was 1 m and each column was packed with 25 l of cation-exchange resin charged with calcium. The solution was provided to pass through the first to forth column at superficial velocity in a column (SV)=0.5. The solution was finally extruded from the column using water as eluent to recover a fraction having a high purity of maltitol. As a result, a high content maltitol syrup was obtained.

The amount of solid component in the resulting high content maltitol syrup was 87.4% when the amount of solid component in the aqueous solution of maltitol supplied to the columns was 100%. Sugar composition in the solid component included 93.5% of maltitol, 1.4% of sorbitol, 5.1% of sugar alcohol which was equal or more than DP3.

Further, the solid component in the other fractions was 12.6% when the amount of solid component in the aqueous solution of maltitol supplied to the column was 100%. Sugar composition in the solid component included 41.9% of maltitol, 24.4% of sorbitol, 33.7% of oligosaccharide alcohol which was equal or more than DP3.

<Third Step>

After the high content maltitol syrup resulting from the second step was condensed to have the concentration of 81%, a portion of the condensed syrup was taken out. Crystalline maltitol powder the amount of which was 0.2% in proportion to the solid component in the syrup was added to the portion under a condition at 66° C. The syrup was slowly stirred and cooled to decrease the temperature from 66° C. to 20° C., spending 24 hours, resulting in magma. The syrup was then subjected to a centrifugal separation. The resulting crystals were rinsed by a small amount of water to recover the crystals.

The purity of crystal was 99.0% and the crystal yield was 33.0% when the solid component in the high content maltitol syrup was 100%.

The concentration of the resulting molasses was 74.9%. The sugar composition included 90.8% of maltitol, 2.0% of sorbitol, 7.2 % of oligosaccharide alcohol which was equal or more than DP3.

Further, the remaining portion of the high content maltitol syrup resulting from the second step was condensed to have the concentration of 95% and then adjusted to have a temperature of 120° C. It was then supplied to a twin-screw extruder for foods (mfg. by NIHON SEIKOSHO K.K., TEX38FSS-20AW-V) at a rate of 20 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 38° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol. The purity of said crystalline mixture solid obtained was 93.5%.

EXAMPLE 8

<First Step>

A commercially available aqueous solution of high purity maltose (mfd. by NIHON SHOKUHIN KAKO K.K., concentration: 60%, sugar composition in the solid component: maltose: 84.6%, glucose: 7.8%, sugar of equal or more than DP3: 7.6%) was reduced under the existence of Raney nickel catalyst at a hydrogen pressure of 100 kg/cm$^2$ and 130° C. for 60 minutes, to obtain aqueous solution of maltitol.

The sugar composition in the solid component of the resulting aqueous solution of maltitol was that maltitol was 84.4%, sorbitol was 8.0%, oligosaccharide alcohol which was equal or more than DP3 was 7.6%.

<Second Step>

The aqueous solution of maltitol resulting from the first step was adjusted to have a concentration of 50% and a temperature of 60° C. 20 l of the solution was supplied to a column. The height of the column was 0.8 m and the column was packed with 20 l of cation-exchange resin charged with sodium. The solution was provided to pass through the column at superficial velocity in a column (SV)=0.4. The solution was finally extruded from the column using water as eluent to recover a fraction having a high purity of maltitol. As a result, a high content maltitol syrup was obtained.

The amount of solid component in the resulting high content maltitol syrup was 80% when the amount of solid component in the aqueous solution of maltitol supplied to the column was 100%. The sugar composition in the solid component of the resulting syrup included 93.5% of maltitol, 1.4% of sorbitol, 5.1% of oligosaccharide alcohol which was equal or more than DP3.

Further, the amount of solid component in the other fractions was 20% when the amount of solid component in the aqueous solution of maltitol supplied to the column was 100%. Sugar composition in the solid component included 48.0% of maltitol, 34.4% of sorbitol, 17.6% of oligosaccharide alcohol which was equal or more than DP3.

<Third Step>

After the high content maltitol syrup resulting from the second step was condensed to have the concentration of 81%, a portion of the condensed syrup was taken out. Crystalline maltitol powder the amount of which was 0.2% in proportion to the solid component in the syrup was added to the portion under a condition at 66° C. The syrup was slowly stirred and cooled to decrease the temperature from 66° C. to 20° C., spending 24 hours, resulting in magma. The syrup was then subjected to a centrifugal separation. The resulting crystals were rinsed by a small amount of water to recover the crystals.

The purity of crystal was 99.0% and the crystal yield was 32.0% when the solid component in the high content maltitol syrup was 100%.

The concentration of the resulting molasses was 75.2%. The sugar composition included 90.9% of maltitol, 2.1% of sorbitol, 7.0% of oligosaccharide alcohol which was equal or more than DP3.

<Fourth Step>

The molasses resulting from the third step was mixed with the remaining portion of the high content maltitol syrup resulting from the second step in a ratio of 1 to 4. The mixture was condensed to have a concentration of 95% and then adjusted to have a temperature of 121° C. It was then supplied to a twin-screw extruder for foods (mfg. by NIHON SEIKOSHO K.K., TEX38FSS-20AW-V) at a rate of 21kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 36° C. during two minutes in which the syrup was processed and discharged from the extruder. The syrup was discharged from twelve extruding pores having a diameter of 4 mm, resulting in maltitol magma.

The maltitol magma was cooled, dried, and crashed to obtain crystalline mixture solid powder containing crystalline maltitol. The purity of crystalline mixture solid obtained was 93.5%.

EXAMPLE 9

<First Step>

A commercially available aqueous solution of high purity maltose having the same sugar composition used in the first step of Example 5 was adjusted to have a concentration of 35%, and then reduced by Raney nickel catalyst, imposed a hydrogen pressure of 100 kg/cm$^2$, under a condition at a temperature of 120° C. for a reaction time of 90 minutes, to obtain aqueous solution of maltitol. The sugar composition in the solid component of the resulting aqueous solution of maltitol was that maltitol was 85.0%, sorbitol was 0.5%, oligosaccharide alcohol which was equal or more than DP3 was 14.5%.

<Second Step>

The aqueous solution of maltitol resulting from the first step was adjusted to have a concentration of 60% and a temperature of 60° C. 20 l of the solution was supplied to a column. The height of the column was 0.8 m and the column was packed with 20 l of cation-exchange resin charged with sodium. The solution was provided to pass through the column at superficial velocity in a column (SV)=0.4. The solution was finally extruded from the column using water as eluent to recover a fraction having a high purity of maltitol. As a result, a high content maltitol syrup was obtained.

The amount of solid component in the resulting high content maltitol syrup was 73% when the amount of solid component in the aqueous solution of maltitol supplied to the column was 100%. The sugar composition in the solid component of the resulting syrup included 94.2% of maltitol, 0.3% of sorbitol, 5.5% of oligosaccharide alcohol which was equal or more than DP3.

Further, the amount of solid component in the other fractions was 27% when the amount of solid component in the aqueous solution of maltitol supplied to the column was 100%. Sugar composition in the solid component included 60.1% of maltitol, 1.0% of sorbitol, 38.9% of oligosaccharide alcohol which was equal or more than DP3.

<Third Step>

After the high content maltitol syrup resulting from the second step was condensed to have the concentration of 84%, a portion of the condensed syrup was taken out. Crystalline maltitol powder the amount of which was 0.2% in proportion to the solid component in the syrup was added to the portion under a condition at 67° C. The syrup was slowly stirred and cooled to decrease the temperature from 66° C. to 20° C., spending 48 hours, resulting in magma. The syrup was then subjected to a centrifugal separation. The resulting crystals were rinsed by a small amount of water to recover the crystals.

The purity of crystal was 98.5% and the crystal yield was 46.2% when the solid component in the high content maltitol syrup was 100%.

The concentration of the resulting molasses was 76.4%. The sugar composition included 90.5% of maltitol, 0.5% of sorbitol, 9.0% of oligosaccharide alcohol which was equal or more than DP3.

<Fourth Step>

The molasses resulting from the third step was mixed with the remaining portion of the high content maltitol syrup resulting from the second step in a ratio of 4 to 6. The mixture was condensed to have a concentration of 95% and then adjusted to have a temperature of 120° C. It was then supplied to a twin-screw extruder for foods (mfg. by NIHON SEIKOSHO K.K., TEX38FSS-20AW-V) at a rate of 20 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 36° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol. The purity of crystalline mixture solid obtained was 92.2% and other component contained in the solid included 0.4% of sorbitol, and 7.4% of oligosaccharide alcohol which was equal or more than DP3.

EXAMPLE 10

<First Step>

A commercially available aqueous solution of high purity maltose having the same sugar composition used in the first step of Example 2 was adjusted to have a concentration of 50%, and then reduced under the existence of Raney nickel catalyst at a hydrogen pressure of 100 kg/cm$^2$ and 130° C. for 1.0 hour, to obtain aqueous solution of maltitol. The sugar composition in the solid component of the resulting aqueous solution of maltitol was that maltitol was 81.0%, sorbitol was 0.5%, oligosaccharide alcohol which was equal or more than DP3 was 18.5%.

<Second Step>

The aqueous solution of maltitol resulting from the first step was adjusted to have a concentration of 60% and a temperature of 60° C. 15 l of the solution was supplied to a column. The height of the column was 0.8 m and the column was packed with 20 l of cation-exchange resin charged with sodium. The solution was provided to pass through the column at superficial velocity in a column (SV)=0.5. The solution was finally extruded from the column using water as eluent to recover a fraction having a high purity of maltitol. As a result, a high content maltitol syrup was obtained.

Sugar composition in the solid component of the resulting high content maltitol syrup included 94.8% of maltitol, 0.2% of sorbitol, 5.0% of oligosaccharide alcohol which was equal or more than DP3.

<Third Step>

After the high content maltitol syrup resulting from the second step was condensed to have the concentration of 84%, a portion of the condensed syrup was taken out. Crystalline maltitol powder the amount of which was 0.2% in proportion to the solid component in the syrup was added to the portion under a condition at 67° C. The syrup was slowly stirred and cooled to decrease the temperature from 67° C. to 20° C., spending 48 hours, resulting in magma. The syrup was then separated by a centrifuge. The resulting crystals were rinsed by a small amount of water to recover the crystals.

The purity of crystal was 98.6% and the crystal yield was 46.5% when the solid component in the high content maltitol syrup was 100%.

The concentration of the resulting molasses was 76.3%. The sugar composition included 91.4% of maltitol, 0.3% of sorbitol, 8.2% of oligosaccharide alcohol which was equal or more than DP=3.

<Fourth Step>

Further, the molasses resulting from the third step was condensed to have a concentration of 95% and then adjusted to have a temperature of 120° C. It was then supplied to a twin-screw extruder for foods (mfg. by NIHON SEIKOSHO K.K., TEX38FSS-20AW-V) at a rate of 20 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol. The purity of crystalline mixture solid obtained was 91.6%. The other component contained in the solid included 0.3% of sorbitol, and 8.1% of oligosaccharide alcohol which was equal or more than DP=3.

EXAMPLE 11

<First Step>

The first step of Example 10 was undertaken, to obtain aqueous solution of maltitol, the sugar composition in the solid component of which aqueous solution was that maltitol was 81.0%, sorbitol was 0.5%, oligosaccharide alcohol which was equal or more than DP3 was 18.5%.

<Second Step>

The aqueous solution of maltitol resulting from the first step was adjusted to have a concentration of 50% and a temperature of 60° C. 15 l of the solution was supplied to a column. The height of the column was 0.8 m and the column was packed with 20 l of cation-exchange resin charged with sodium. The solution was provided to pass through the column at superficial velocity in a column (SV)=0.5. The solution was finally extruded from the column using water as eluent to recover a fraction having a high purity of maltitol. As a result, a high content maltitol syrup containing 93.2% of maltitol, 0.3% of sorbitol, 6.5% of oligosaccharide alcohol which was equal or more than DP3 was obtained.

The amount of solid component in the resulting high content maltitol syrup fraction was 80% when the amount of solid component in the aqueous solution of maltitol supplied to the column was 100%.

<Third Step>

After the high content maltitol syrup resulting from the second step was condensed to have the concentration of 75%, a portion of the condensed syrup was taken out. Crystalline maltitol powder the amount of which was 0.3% in proportion to the solid component in the syrup was added to the portion under a condition at 65° C. The syrup was slowly stirred and cooled to decrease the temperature from 65° C. to 20° C., spending 24 hours, resulting in magma. The syrup was then separated by a centrifuge. The resulting crystals were rinsed by a small amount of water to recover the crystals.

The purity of crystal was 99.2% and the crystal yield was 26.8% when the solid component in the high content maltitol syrup was 100%.

The concentration of the resulting molasses was 69.8%. The sugar composition included 91.0% of maltitol, 0.3% of sorbitol, 8.6% of oligosaccharide alcohol which was equal or more than DP=3.

<Fourth Step>

Further, the molasses resulting from the third step was condensed to have a concentration of 95% and then adjusted to have a temperature of 120 ° C. It was then supplied to a twin-screw extruder for foods (mfg. by NIHON SEIKOSHO K.K., TEX38FSS-20AW-V) at a rate of 20 kg/hour. Crystalline mixture solid powder containing crystalline maltitol the amount of which was about 30% in proportion to the solid component in the syrup was added as a seed crystal to the syrup. The syrup was cooled while being kneaded at a speed of 60 rpm so as to decrease the temperature of the syrup to 40° C. during two minutes in which the syrup was processed and discharged from the extruder. The syrup was discharged from twelve extruding pores having a diameter of 4 mm, resulting in maltitol magma.

The maltitol magma was cooled, dried and crashed to obtain crystalline mixture solid powder containing crystalline maltitol. The purity of crystalline mixture solid obtained was 89.4%. The other component contained in the solid included 0.3% of sorbitol, and 8.3% of oligosaccharide alcohol which was equal or more than DP3.

EXAMPLE 12

After the fraction having a high purity of maltitol resulting from the second step in Example 9 was condensed to have the concentration of 75% and heated to have a temperature of 100° C., the fraction was supplied to massecuite preparative pool, and then cooled down with stirring to 15° C., spending 30 minutes. Crystalline maltitol fine powder the amount of which was 2% in proportion to the solid component in the aqueous solution of maltitol was added to the fraction. By continuing to stir the fraction for 5 hours, maltitol massecuite having 35% of suspended crystal was obtained.

Further, maintaining the massecuite at a temperature of 15° C., the massecuite was supplied to the spray-dryer of an atomizer type having an inner diameter of 8 m, while respectively controlling the condition of temperature for supplying the massecuite at a temperature of 70° C. and that for exiting the massecuite at a temperature of 40° C. It was then spray-dried. As a result, maltitol powder was obtained.

The powder deposited on the floor of spray-dryer had water content of 4.8%. The powder was matured for 5 hours at a temperature of 40° C., and dried in a dryer at a temperature of 95° C., for 1 hour, resulting in a crystalline mixture solid containing crystalline maltitol of a good flowability containing water content of 0.3%, and having an angle of repose being 32 degree and a purity of 94.1%.

EXAMPLE 13

The molasses resulting the third step of Example 6 was subjected to the step of Example 12 to obtain maltitol powder. The powder deposited on the floor of spray-dryer had water content of 4.6%. As discussed in Example 12, the powder was matured and dried, resulting in a crystalline mixture solid containing crystalline maltitol of a good flowability containing water content of 0.3%, and having an angle of repose being 32 degree and a purity of 95.3%.

COMPARATIVE EXAMPLE 1

A commercially available maltose syrup (mfd. by NIHON SHOKUHIN KAKO K.K., concentration: 60%, and maltose purity: 62%) was hydrogenated under the existence of catalyst and subjected to a chromatographic separation according to the TOKKYO KOUKOKU KOHO (Patent Publication for Opposition), Heisei 2(1990)-11599 to obtain a condensed fraction of maltitol. The sugar composition in the condensed fraction was that sorbitol was 1.4%, maltitol was 90.5%, oligosaccharide alcohol which was DP3 was 7.5%, and oligosaccharide alcohol which was equal or more than DP=4 was 0.6%.

After the fraction was condensed to have a concentration of 90%, 0.1% of a seed crystal having a maltitol purity of 99% was added to 51 kg of the condensed fraction at a temperature of 75° C. The fraction was further cooled, spending 50 hours to have a temperature of 25° C. so that the fraction was cooled down 1° C. per hour by gently stirring the fraction so as to obtain a crystalline slurry. This slurry was centrifuge separated, and rinsed by a small amount of water, resulting in 30.3 kg maltitol crystalline containing water content of 6.1% and a purity of 99%. (The yield was 62%: the ratio by weight of the dried crystalline maltitol in proportion to the dried solid component in the starting material.) The components other than maltitol included 0.6% of sorbitol and 0.4% of oligosaccharide alcohol which was equal or more than DP=3.

The molasses which was by-product of the above process had a concentration of 71.2%. The sugar composition of the molasses included 2.7% of sorbitol, 76.6% of maltitol, and 20.7% of oligosaccharide alcohol which was equal or more than DP=3. Although the molasses was condensed to have a concentration of 95%, and then subjected to the third step of Example 1 for preparing a crystalline mixture solid containing crystalline maltitol, maltitol magma could not be obtained. The molasses could neither be solidified nor result in any crystalline maltitol mixture solid.

EFFECT OF INVENTION

As discussed above, this invention can manufacture both crystalline maltitol and crystalline mixture solid containing crystalline maltitol to which high value can be added at the same time from inexpensive maltose syrup having a maltose purity of 81 to 90% in the solid component which can be manufactured by using enzyme of general use such as α-amylase, β-amylase, and pullulanase, without using any very expensive enzyme with a peculiar use such as isoamylase.

Further, the process of this invention results in very little by-product to which high value cannot be added, and the resulting product of this invention is effectively chromatographically separated, resulting in a low condensing step cost. Further, the molasses resulting from the step for manufacturing crystalline maltitol can be also used to manufacture crystalline mixture solid containing crystalline maltitol. In short, this invention is economically advantageous to conventional process in manufacturing crystalline maltitol and crystalline mixture solid containing crystalline maltitol.

We claim:

1. A process for manufacturing crystalline maltitol and a crystalline mixture solid containing crystalline maltitol from the same raw material comprising, in sequence:
    a) hydrogenating a syrup having a concentration of 30–70% solids by weight and a maltose content of 81–90% by weight of solids in the presence of a catalyst which is not isoamylase to obtain a corresponding syrup of sugar alcohol, and
    b) chromatographically separating said syrup of sugar alcohol by supplying said syrup of sugar alcohol to a column packed with a cation-exchange resin to obtain a high content maltitol syrup fraction having a maltitol purity of 92 to 99.9% by weight based on solids, and
    c) condensing said high content maltitol syrup, and
        i. crystallizing a first part of said condensed high content maltitol syrup in the presence of first seed crystal to form a crystalline maltitol, and
        ii. spray-drying or kneading while cooling, a second part of said condensed high content maltitol syrup in the presence of second seed crystal to form a crystalline mixture solid containing crystalline maltitol.

2. The process as defined in claim 1
    wherein said cation-exchange resin is charged with either calcium or sodium ions, and
    wherein said separating step is performed by a batch process.

3. The process as defined in claim 2
    wherein said maltitol purity of said high content maltitol syrup fraction is 94 to 99.9%.

4. The process as defined in claim 1
    wherein said step c)ii. comprises kneading while cooling.

5. A process for manufacturing crystalline maltitol and a crystalline mixture solid containing crystalline maltitol from the same raw material comprising, in sequence:
    a) hydrogenating a syrup having a concentration of 30–70% solids by weight and a maltose content of 81–90% by weight of said solids in the presence of a catalyst which is not isoamylase to obtain a corresponding syrup of sugar alcohol,
    b) chromatographically separating said syrup of sugar alcohol by supplying said syrup of sugar alcohol to a column packed with a cation-exchange resin to obtain a high content maltitol syrup fraction having a maltitol purity of 92 to 99.9% by weight based on solids, and
    c) condensing said high content maltitol syrup and crystallizing said condensed high content maltitol syrup to form a crystallized maltitol and separating and collecting said crystallized maltitol from a mother liquor, and
    d) adding high content maltitol syrup fraction produced from said separating step to said mother liquor from said crystallizing step to form a mixture, and
    condensing said mixture and spray-drying or kneading while cooling said mixture in the presence of a seed crystal to obtain a crystalline mixture solid containing crystalline maltitol.

6. The process as defined in claim 5
    wherein said cation-exchange resin is charged with either calcium or sodium ions, and
    wherein said separating step is performed by a batch process.

7. The process as defined in claim 5
    wherein said maltitol purity of said high content maltitol syrup fraction is 94 to 99.9%.

8. A process for manufacturing crystalline maltitol and crystalline mixture solid containing crystalline maltitol from the same raw material comprising, in sequence:
    a) hydrogenating a syrup having a concentration of 30–70% solids by weight and a maltose content of 81–90% by weight of said solids in the presence of a catalyst which is not isoamylase to obtain a corresponding syrup of sugar alcohol,
    b) chromatographically separating said syrup of sugar alcohol by supplying said syrup of sugar alcohol to a column packed with a cation-exchange resin to obtain a high content maltitol syrup fraction having a maltitol purity of 92 to 99.9% by weight based on solids, and
    c) condensing said high content maltitol syrup and crystallizing said condensed high content maltitol syrup to form a crystallized maltitol and separating and collecting said crystallized maltitol from a mother liquor, and
    crystallizing said mother liquor in the presence of a seed crystal to form a crystalline mixture solid containing crystalline maltitol.

9. The process as defined in claim 8
    wherein said cation-exchange resin is charged with either calcium or sodium ions, and
    wherein said separating step is performed by a batch process.

10. The process as defined in claim 8
    wherein said maltitol purity of said high content maltitol syrup fraction is 94 to 99.9%.

* * * * *